US009221803B2

(12) United States Patent
Mena Cervantes et al.

(10) Patent No.: US 9,221,803 B2
(45) Date of Patent: *Dec. 29, 2015

(54) ASPHALTENE-DISPERSING/INHIBITING ADDITIVE BASED ON OXAZOLIDINES DERIVED FROM POLYALKYL OR POLYALKENYL N-HYDROXYALKYL SUCCINIMIDES

(75) Inventors: Violeta Yasmin Mena Cervantes, Mexico City (MX); Simon Lopez Ramirez, Mexico City (MX); Luis Silvestre Zamudio Rivera, Mexico City (MX); Youri Douda, Mexico City (MX); Mario Alberto Guzman Vega, legal representative, Mexico City (MX); Marcelo Lozada Y Cassou, Mexico City (MX); Adela Morales Pacheco, Mexico City (MX); Hiram Issac Beltran Conde, Mexico City (MX); Raul Hernandez Altamirano, Mexico City (MX); Eduardo Buenrostro Gonzalez, Mexico City (MX); Mariana Barcenas Castaneda, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 881 days.

This patent is subject to a terminal disclaimer.

(21) Appl. No.: 12/808,449
(22) PCT Filed: Nov. 4, 2008
(86) PCT No.: PCT/MX2008/000150
§ 371 (c)(1),
(2), (4) Date: Jun. 16, 2010
(87) PCT Pub. No.: WO2009/078694
PCT Pub. Date: Jun. 25, 2009

(65) Prior Publication Data
US 2011/0162558 A1      Jul. 7, 2011

(30) Foreign Application Priority Data
Dec. 18, 2007   (MX) .................... MX/a/2007/016265

(51) Int. Cl.
*C07D 413/06* (2006.01)
*C07D 207/412* (2006.01)
*C07D 263/04* (2006.01)
*C10L 1/233* (2006.01)
*C10L 10/18* (2006.01)
*C10L 1/224* (2006.01)
*C10L 1/2383* (2006.01)

(52) U.S. Cl.
CPC .......... *C07D 413/06* (2013.01); *C07D 207/412* (2013.01); *C07D 263/04* (2013.01); *C10L 1/233* (2013.01); *C10L 10/18* (2013.01); *C10L 1/224* (2013.01); *C10L 1/2383* (2013.01)

(58) Field of Classification Search
CPC ............. C07D 413/06; C07D 207/412; C07D 263/04; C10L 1/233; C10L 10/18; C10L 1/224; C10L 1/2383
USPC .......................... 516/20, 43; 106/506; 44/341
See application file for complete search history.

(56) References Cited

U.S. PATENT DOCUMENTS 4,049,564 A * 9/1977 Ryer et al. .................... 508/221
4,277,353 A * 7/1981 Deen et al. .................... 508/270
(Continued)

FOREIGN PATENT DOCUMENTS

EP       1359208       11/2003
MX    PA01013139       6/2003
WO   WO 2008/130214 A1 * 10/2008

OTHER PUBLICATIONS

O'Neil, Maryadele J. et al. (©2006, 2010), The Merck Index-An Encyclopedia of Chemicals, Drugs, and Biologicals (14th Ed.- Vers 14.6), Merck Sharp & Dohme Corp., Whitehouse Station, NJ (Knovel Date: Dec. 1, 2007), Entries Kerosene Xylene, @ http://knovel.com/web/portal/browse/display?_EXT_KNOVEL_DISPLAY_bookid=1863&VerticalID=0 (Downloaded Sep. 29, 2012).*

*Primary Examiner* — Daniel S Metzmaier
(74) *Attorney, Agent, or Firm* — Dickinson Wright PLLC

(57) ABSTRACT

The present invention relates to formulations of asphaltenes' inhibitor-dispersant additives based on oxazolidine derived from polyalkyl or polyalkenyl N-hydroxyalkyl succinimides. Said formulations can contain inert organic solvents, preferably including: toluene, mixtures of xylene, o-xylene, p-xylene, kerosene, turbo-fuel; or inert hydrocarbon solvents having boiling points within the range of gasoline and diesel; or inert hydrocarbon or organic solvents having a boiling point within a range from 75 to 300° C. The ratio in weight of inert organic solvents to additive that prevents and controls the precipitation and deposition of asphaltenes ranges from 1:9 to 9:1, preferably from 1:3 to 3:1.

24 Claims, 5 Drawing Sheets

(56) References Cited

U.S. PATENT DOCUMENTS

| | | | |
|---|---|---|---|
| 4,471,091 A | 9/1984 | Hayashi | |
| 5,466,387 A * | 11/1995 | Pianta et al. | 508/232 |
| 5,962,378 A | 10/1999 | Tiffany et al. | |
| 6,147,036 A * | 11/2000 | Baker | 508/454 |
| 6,313,367 B1 | 11/2001 | Breen | |
| 8,063,004 B2 * | 11/2011 | Goldman | C09K 8/524 208/24 |
| 2006/0035793 A1 * | 2/2006 | Goldman | C09K 8/524 508/433 |
| 2010/0107478 A1 * | 5/2010 | Zamudio Rivera et al. | 44/341 |

* cited by examiner

ASPHALTENE-DISPERSING/INHIBITING ADDITIVE BASED ON OXAZOLIDINES DERIVED FROM POLYALKYL OR POLYALKENYL N-HYDROXYALKYL SUCCINIMIDES

TECHNICAL FIELD OF THE INVENTION

The present invention relates to formulations of asphaltene-dispersing/inhibiting additives based on oxazolidines derived from polyalkyl or polyalkenyl N-hydroxyalkyl succinimides.

BACKGROUND OF THE INVENTION

Petroleum in its natural state is considered a colloidal system constituted by four well defined organic fractions: 1) Saturated, 2) Aromatic, 3) Resins, and 4) Asphaltenes.

Asphaltenes are typically defined as the fraction of crude oil that is insoluble in low molecular weight aliphatic solvents such as n-pentane and n-heptane, but soluble in toluene, and that exist in the form of colloidal dispersions stabilized by resins.

From the structural point of view, asphaltenes are molecular aggregates of polyaromatic rings having small quantities of heteroatoms (sulfur, nitrogen and oxygen), traces of metal (iron, nickel and vanadium), linear branches having paraffinic characteristics and that remain primarily bound by $\pi$-$\pi$-type supramolecular interactions. Said structural characteristics entail that asphaltenes be the most polar fraction in crude oil and that they tend to precipitate upon abrupt temperature, pressure, or composition changes occurring at the extraction, transportation, or processing of crude oil.

The phenomenon of asphaltenes' precipitation in crude oil occurs when, at favorable temperature, pressure, and composition conditions, small asphaltene particles having low molecular weight associate, grow, and generate large and heavy asphaltene aggregates that become insoluble in the media. The large weight and the polar nature of these asphaltenes result in them diffusing towards the bottom of the oilfield's, pipeline or equipment, and adhering tightly to their walls. This phenomenon is known as asphaltene deposition.

Asphaltene deposition is directly related with: 1) Damage to the formation in oilfields, 2) Fouling and clogging of the hydrocarbon production wells and transportation ducts, and 3) Fouling occurring in the crude oil refining plants. Such problems cause great yearly losses to the oil industry.

Traditionally, in the petroleum industry, the fouling and clogging problems caused by the deposition of asphaltenes have been controlled by means of the use of asphaltene inhibitors and/or dispersants, which are comprised by two essential parts known as head and tail.

The head (the philic part) is a polar group whose function is to interact with the aromatic rings or the polar groups of the asphaltenes, whereas the tail (the phobic part) is an aliphatic chain that can be linear or branched and whose function consists in forming an esteric chain, which prevents the asphaltene molecules from getting too close to each other.

FIG. (1) shows that, by means of theoretical Monte Carlo simulations, it is possible to explain the way that the asphaltene aggregation process is controlled by the use of asphaltene inhibitors-dispersants.

In FIG. (1), the squares represent the asphaltenes' polar group (active site), the black and white circles represent the inhibitor-dispersant (head and tail, respectively), and the light-gray colored circles are the media (solvent). In our calculations we have assumed that the inhibitor-dispersant efficiency is directly related in a linear fashion with the concentration of asphaltene active sites "covered" (reacted) by the head of the inhibitor. The simulation calculation was carried out for two inhibitor-dispersant concentrations (A and B), where the concentration of A is lower than the concentration of B. In the simulation, two asphaltenes tending to agglomerate are represented as two surfaces having active sites at a certain H distance between them. These two parallel-located surfaces are immersed in a solvent to which a certain inhibitor-dispersant concentration is added in order to locally analyze its performance (head- and active site-association of an asphaltene).

As shown in part a of FIG. (1) (inhibitor concentration A), the head drives the inhibitor-dispersant to shift and bind to the asphaltene surface's active sites, where more than 50% of the inhibitors placed in the system remain adsorbed; additionally, it can be appreciated how the tail blocks some active sites, producing an steric effect.

However, in part b of FIG. (1) (concentration B) it can be observed that, upon increasing the inhibitor-dispersant concentration, the formation of a micelle-aggregate comprised by inhibitor-dispersant molecules occurs, and the affinity of the head to link with an active-site of the asphaltene markedly decreases, leaving its surface almost free.

Hence the importance that the adequate selection of the functional groups conforming the head of the inhibitor-dispersant molecule has, as well as the care given to the design of its structure, in order that the head links with the asphaltene active-site, and the tail forms an esteric barrier, while minimizing unwanted supramolecular interactions, such as the formation of inhibitor-dispersant micelles at the same time.

As important examples in the literature, mentioning the development of chemical compounds and their applications in crude oil in order to inhibit or disperse asphaltene deposits, we can mention the international patents: U.S. Pat. Nos. 7,122,113 B2, 7,122,112 B2, 7,097,759 B2, 6,946,524 B2, 6,313,367 B1, 6,204,420 B1, 6,180,683 B1, 6,063,146, 6,048,904, 5,504,063, 5,494,607, 5,466,387, 5,388,644 y 5,021,498.

The U.S. Pat. No. 7,122,113 B2 refers to the use of dendrimeric compounds to solubilize asphaltenes present in a hydrocarbon mixture. Preferably, the dendrimeric compound is a hyperbranched amide polyester, preferably constructed based on succinic anhydride, diisopropanol amine, and functionalized with polyisobutenil succinic anhydride.

The U.S. Pat. No. 7,122,112 B2 refers to the development of compounds having the structural formula:

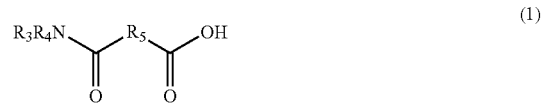

(1)

containing specifically carboxyl and amide groups within their structure, and their application as asphaltene dispersants in crude oil.

Within the structural formula (1), $R_5$ is a difunctional alkyl group that can range from $C_1$ to $C_{70}$, and $R_3$ and $R_4$ are independent radicals that can be represented by aryl, alkyl, alkylaryl, heterocyclyl groups, or hydrogen. The patent also indicates that this type of compounds increases demulsibility, and reduces viscosity, sediment formation, fouling of surfaces, and corrosion.

The U.S. Pat. No. 7,097,759 B2 refers to the development of compounds having the structural formula:

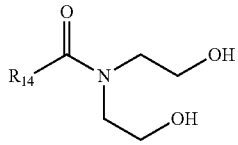

(2)

specifically having in their structure a carbonyl, thiocarbonyl, or imine group, and their application as asphaltene dispersants in crude oil. Within the structural formula (2), $R_{14}$ is an alkyl group that can range from $C_{15}$ to $C_{21}$. The patent also indicates that this type of compounds increases demulsibility, and reduces viscosity, sediment formation, fouling of surfaces, and corrosion.

The U.S. Pat. No. 6,946,524 B2 refers to a process to produce polyesteramides, by reacting a polyisobutylene with a first agent selected from the group consisting in monounsaturated acids having from 3 to 21 carbon atoms and derivatives thereof, and a second agent selected from the group comprised by monoethanolamine and alkylamines having the structural formula:

 (3)

wherein R represents an alkyl group having from 1 to 4 carbon atoms. The resulting polyesteramides are used as asphaltene stabilizers in crude oil and crude oil derivatives.

The U.S. Pat. No. 6,313,367 B1 patent, mentions that several esters and ethers reaction products are excellent asphaltene inhibitors or dispersants and can be used in hydrocarbons such as crude oil. The asphaltene-inhibitor compounds can be: 1) esters formed from the reaction of polyhydric alcohols with carboxylic acids, 2) ethers formed from the reaction of glycidyl ethers or epoxydes with polyhydric alcohols, and 3) esters formed from the reaction of glydicyl ethers or epoxides with carboxylic acids.

The U.S. Pat. No. 6,204,420 B1 mentions the development of a new formulation where the asphaltene-dispersant action of carboxylic acids can be extensively enhanced by the addition of relatively small amounts of esters derived from alkyl phosphoric acids. The formulation comprises: A) 5 to 99% in weight of a carboxylic acid having more than 4 carbon atoms, an ethercarboxylic acid bearing $C_{18}$-$C_{22}$ alkylic, $C_{18}$-$C_{22}$ alkenylic, or $C_6$-$C_{18}$ alkylarylic substituents, an amide-carboxylic acid or a mixture thereof, and B) 1 to 95% in weight of a mono- or di-phosphoric ester or a mixture thereof, which is substituted by a $C_{18}$-$C_{22}$ alkylic, a $C_{18}$-$C_{22}$ alkenylic, a $C_6$-$C_{18}$ alkylarylic or an alkoxylated group, wherein the sum of A and B is 10% in weight.

The U.S. Pat. No. 6,180,683 B1 mentions the development of a new formulation having a synergistic effect as an asphaltene dispersant. The formulation comprises 5 to 95% of a compound A having the structural formulae I or II:

Formula I

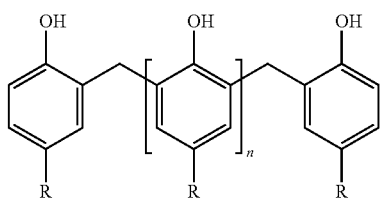

(4)

Formula II

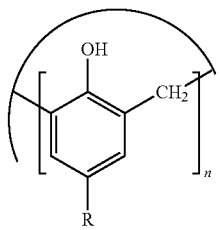

and with 5 to 95% in weight of a compound B having the structural formula III:

Formula III

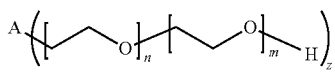

(5)

The formulation is an excellent asphaltene dispersant in crude oil and crude oil-derived products.

Within the structural formulae I and II on (4), n is within the range from 2 to 12, preferably from 5 to 9, and R is a $C_3$-$C_{24}$, preferably a $C_4$-$C_{12}$ alkyl group, particularly isononil, isobutyl or amyl, or a $C_6$-$C_{12}$ aryl group or a $C_7$-$C_{12}$ alkylaryl group or an hydroxyaryl group.

Within the structural formula III in (5), n and m are independent from each other, and are numbers within the range from 0 to 120, preferably from 5 to 80, with the sum of m and n yielding at least 5. Z is an integer ranging from 1 to 4, preferably 4, and A is a radical containing amine groups within its structure.

The U.S. Pat. No. 6,063,146 refers to the use of ethercarboxylic acids having the structural formula:

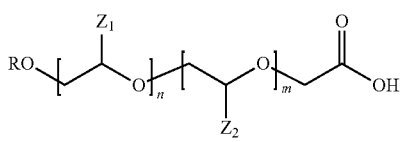

(6)

as asphaltene-dispersants in crude oil and crude oil-derived products.

Within the structural formula (6), R is a $C_6$-$C_{22}$, preferably $C_9$-$C_{18}$ alkyl group, or a $C_6$-$C_{20}$ alkylaryl group. $Z_1$ and $Z_2$ are independent from each other, and can be H or a methyl group, preferably H. n and m are independent numbers between each other, and lie between the range from 0 to 20, the total of n and m falling within the range from 1 to 20, preferably from 1.5 to 8.

The U.S. Pat. No. 6,048,904 mentions the use of branched alkylaromatic sulfonic acids having the structural formula:

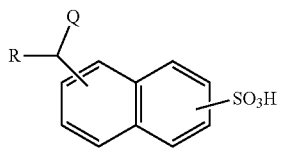

(7)

used as asphaltene dispersants in crude oil and crude oil-derived products.

Within the structural formula (7), R and Q are alkyl chains having a length ranging from 16 to 30 carbon atoms with at least one branch of a methyl group or longer alkyl groups.

The U.S. Pat. No. 5,504,063 mentions that a formulation formed by the product of the condensation reaction of a fatty acid, an alkylene amine, and one or more polar aprotic solvents having a high dielectric constant is useful for removing and inhibiting asphaltene deposits from wells, ducts, and associated equipment.

The U.S. Pat. No. 5,494,607 mentions that alkyl mono- or di-substituted phenol-formaldehyde and/or alkyl monosubstituted phenol-polyethylenepolyamine-formaldehyde resins are useful as asphaltene dispersants in crude oil and crude oil-derived products. Said resins have an average molecular weight ranging from 1000 to 20000 and the substituent alkyl contains from 4 to 24 carbon atoms and can be linear or branched.

The U.S. Pat. No. 5,466,387 mentions that crude-soluble additives with dispersing properties are prepared by reacting an alkyl or alkenyl disuccinimide with an unsaturated bicarboxylic aliphatic acid or the corresponding acid. The reaction is carried out at a temperature ranging from 130 to 170° C.; the anhydride-to-disuccinimide molar ratio ranges between 1.05 and 1.95.

The U.S. Pat. No. 5,388,644 mentions a method to reduce, preferably to prevent, the precipitation of asphaltenes in crude oil. In a first stage, the crude oil comes into contact in the drill with at least an N,N-dialkylamide derived from a fatty acid having from 8 to 22 carbon atoms. In a second stage, the precipitation is reduced during the miscible injection in a recuperation process enhanced by adding at least one N,N-dialkylamide derived from a fatty acid having from 8 to 22 carbon atoms to the injected solvent. The N,N-dialkylamides derived from fatty acids are represented by the structural formula:

$R_3C(O)—N(R_1)(R_2)$        (8)

Within the structural formula on (8), $R_1$ is a substituted or non-substituted alkyl group located between $C_1$-$C_6$, $R_2$ is a substituted or non-substituted alkyl group located between $C_1$-$C_6$, and $R_3(C(O)$ is a residue of a substituted or non-substituted fatty acid with 8 to 22 carbon atoms.

The U.S. Pat. No. 5,021,498 mentions that a mixture of an alkyl substituted phenol-formaldehyde resin with a hydrophilic-lipophilic vinylic polymer acts as an asphaltene and asphalt dispersant in crude oil. The alkyl substituted phenol-formaldehyde resin has an average molecular weight ranging from 1000 to 20000, the alkyl substituent contains from 4 to 24 carbon atoms and it may be linear or branched, and the weight percentage of said resin in the mixture can range from 10 to 100. The weight percent of the hydrophilic-lipophilic vinylic polymer in the mixture can range from 10 to 100.

The present invention markedly surpasses the aforementioned references since it consists of additive formulations containing as their main component an oxazolidine derived from polyalkyl or polyalkenyl N-hydroxyalkyl succinimides, capable of acting both as asphaltene inhibitors and dispersants to be used in crude oil or products derived thereof in order to control fouling and/or clogging problems occurring in production, transportation, refining, and storage processes related with the petroleum industry. These formulations distinguish themselves with respect to the commercial products evaluated for this double function because, even when one of them showed a comparable or slightly superior capability in the dispersion tests, it was clearly surpassed, as were both the other products, in the precipitation and deposition inhibition tests.

BRIEF DESCRIPTION OF THE DRAWINGS

The following is a brief description of the figures referred to in the text.

Figure 1:
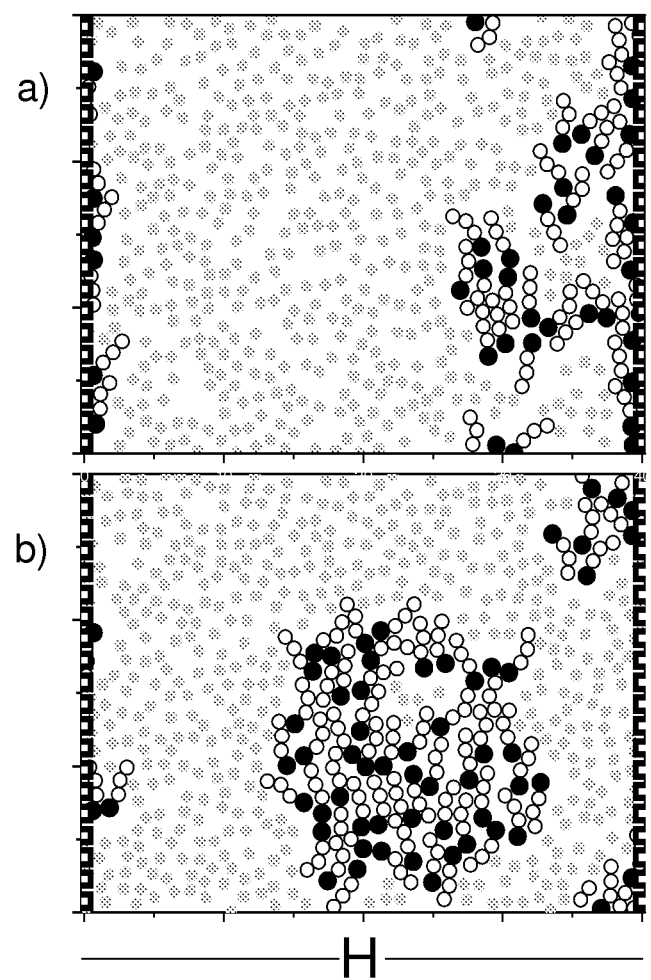
FIG. 1 illustrates the explanation that can be given, by means of Monte Carlo theoretical simulations, on the way the asphaltene aggregation process is controlled by the use of inhibitors-dispersants. Of note, in this figure, letter H represents the distance between two asphaltene active sites, and a and b represent the two concentrations of the inhibitor, the black circles represent the head, the white ones the tail, and the grey ones, the solvent, while the squares drawn at the left and right sides of the figure represent the active site.
Figure 2:
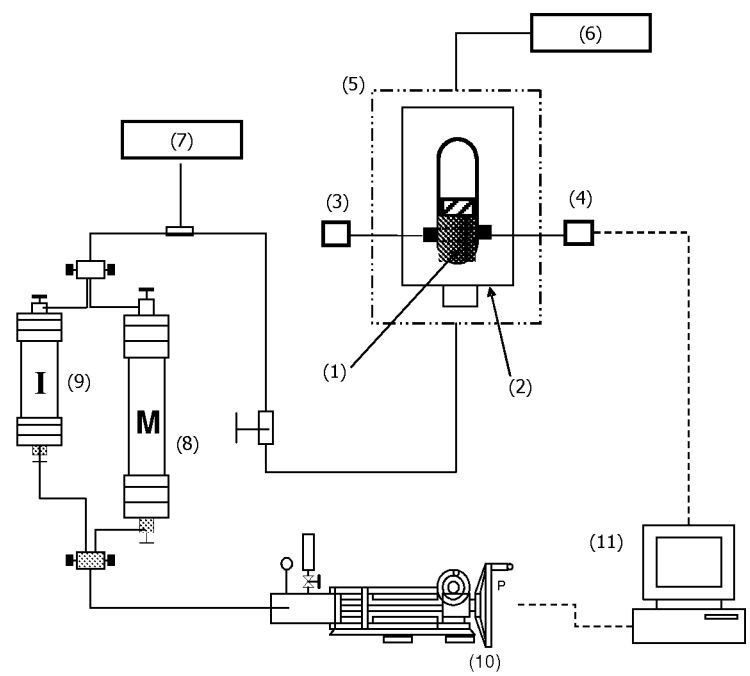
FIG. 2 illustrates the device used to perform the measurement test of the onset of the asphaltene precipitation by pressure changes to bottom-of-well temperature and pressure conditions.

The numbers indicated in FIG. 2 correspond to the following components: (1) Preserved live crude petroleum sample. (2) Variable volume balance visual cell. (3) Light source. (4) Detector. (5) Air thermal bath. (6) Temperature meter. (7) Pressure meter. (8) High-pressure cylinder with preserved sample. (9) High-pressure cylinder with inhibitor. (10) Computerized pump. (11) Computer.

Figure 3:
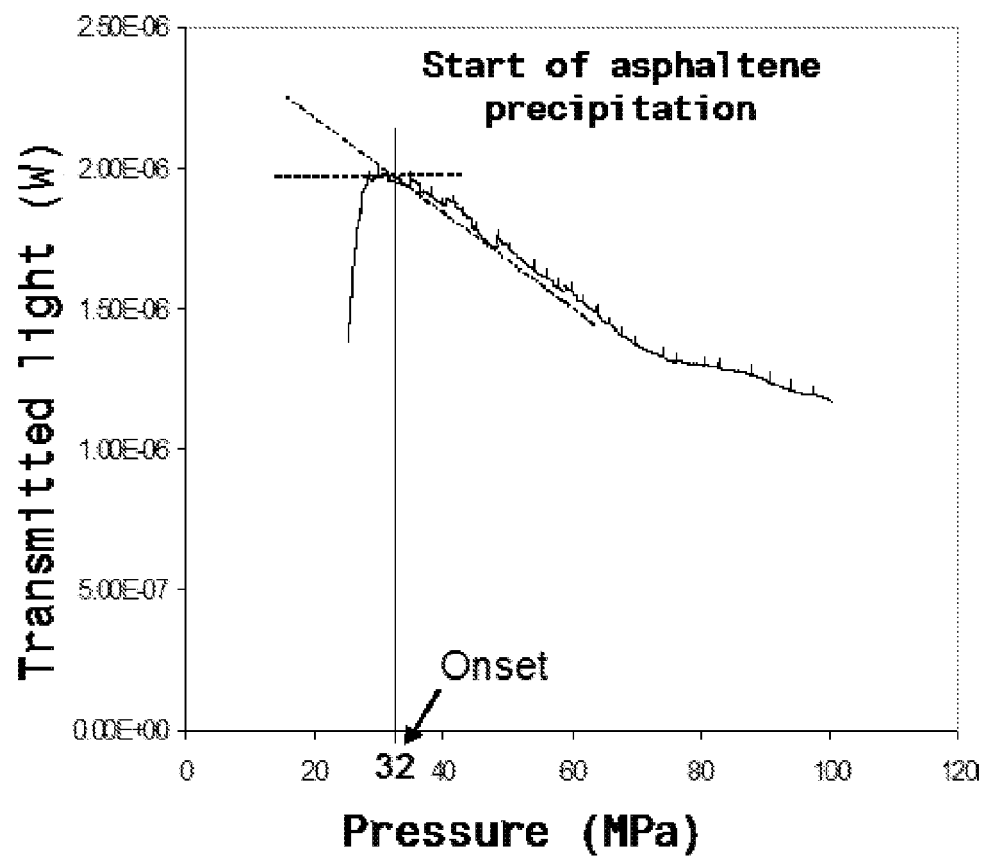

FIG. 3 illustrates the transmitted light potency vs. generated pressure graph generated in the computer screen during the test measuring the onset of the precipitation of asphaltenes by pressure change to bottom-of-well temperature and pressure conditions. The graph indicates the point representing the inset of the asphaltenes' precipitation.

Figure 4:
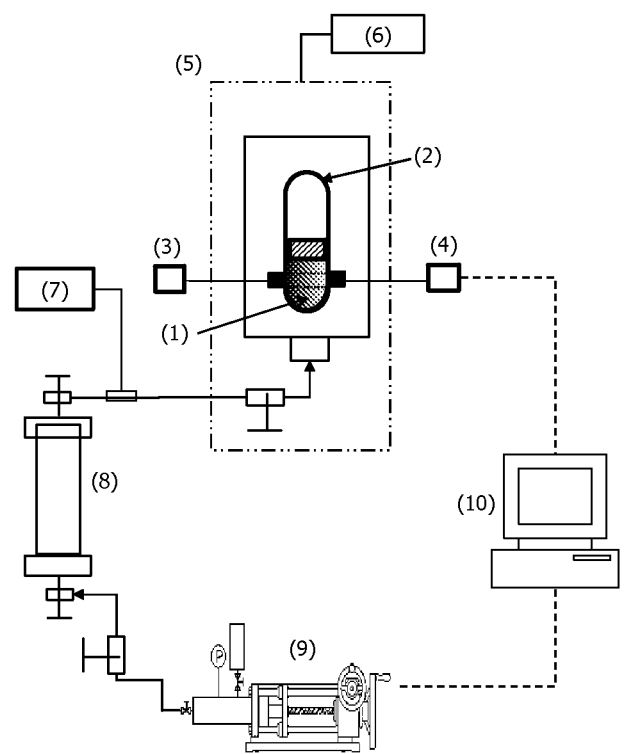

FIG. 4 illustrates the device used to perform the test that measures the onset of the asphaltenes' precipitation by adding a precipitant at room temperature and pressure conditions.

The numbers indicated in FIG. 4 correspond to the following components: (1) Sample of the crude sample and precipitant. (2) Variable volume balance visual cell. (3) Source of light. (4) Detector. (5) Air thermal bath. (6) Temperature meter. (7) Pressure meter. (8) Cylinder with precipitant. (9) Computerized pump. (10) Computer.

Figure 5:
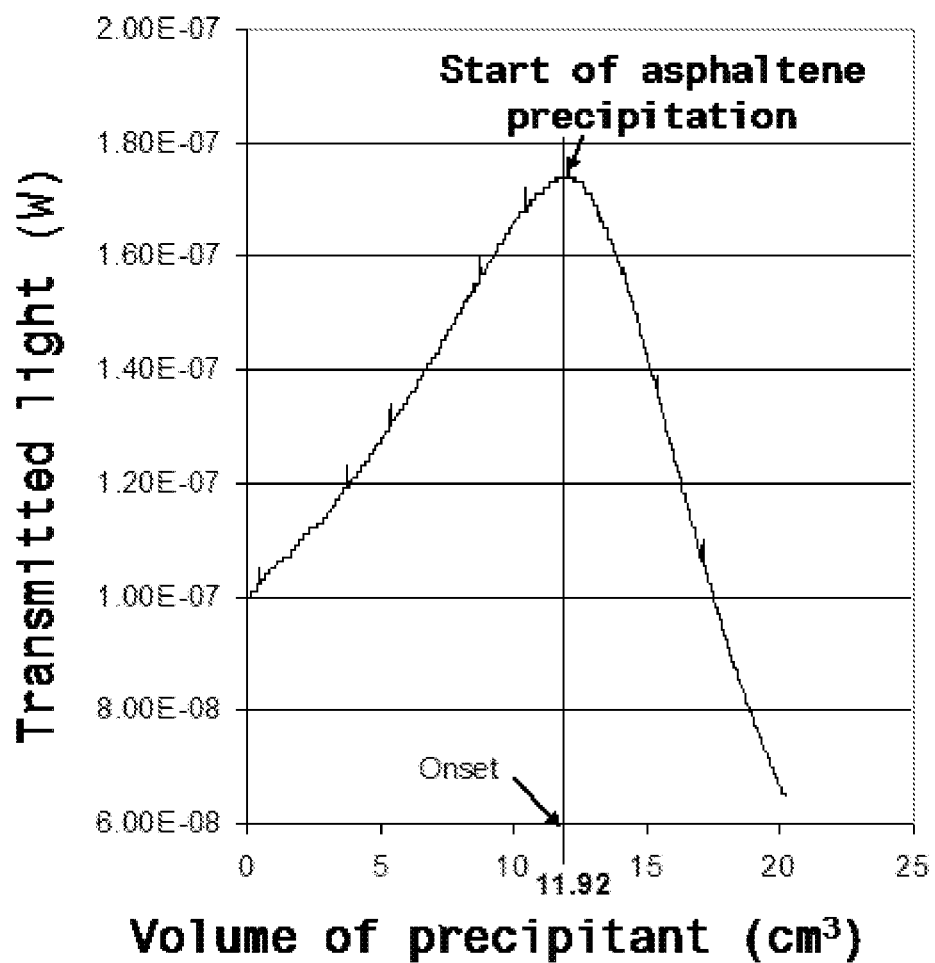

FIG. 5 illustrates the transmitted light potency vs. pressure graph generated in the computer screen during the test to measure the onset of the precipitation of asphaltenes by adding a precipitant at ambient temperature and pressure conditions. The graph indicates the point representing the onset of the asphaltenes' precipitation.

DETAILED DESCRIPTION OF THE INVENTION

It has been discovered that oxazolidines derived from polyalkyl or polyalkenyl N-hydroxyalkyl succinimides having the structural formula illustrated in (9) are highly efficient as asphaltene dispersants-inhibitors in crude oil:

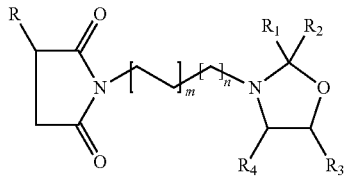

(9)

In the structural formula (9), R is a polyalkyl or polyalkenyl group having an average molecular weight ranging from 450 to 5000 Daltons, m is an integer with values ranging from 1 to 5; m is an integer with values ranging from 0 to 1, and $R_1$, $R_2$, $R_3$ y $R_4$ are independent radicals that can be represented by the groups —H, —$CH_2(CH_2)_4B$, —$C_6H_3DE$ or —$C_{10}H_4FG$; wherein A is an integer ranging from 0 and 8, B is a group selected among —H, —$NH_2$, —OH, —COOH, and D, E, F and G are independent radicals selected among the groups —H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_6$—COOH, —$SO_3$.

The oxazolidines derived from polyalkyl or polyalkenyl N-hydroxyalkyl succinimides having the structural formula shown in (9) were synthesized according to the procedure established in the patent application submitted to the Mexican Institute of Industrial Property, on Apr. 18, 2007, Folio MX/E/2007/0238. The corresponding synthesis pathway is shown in (10).

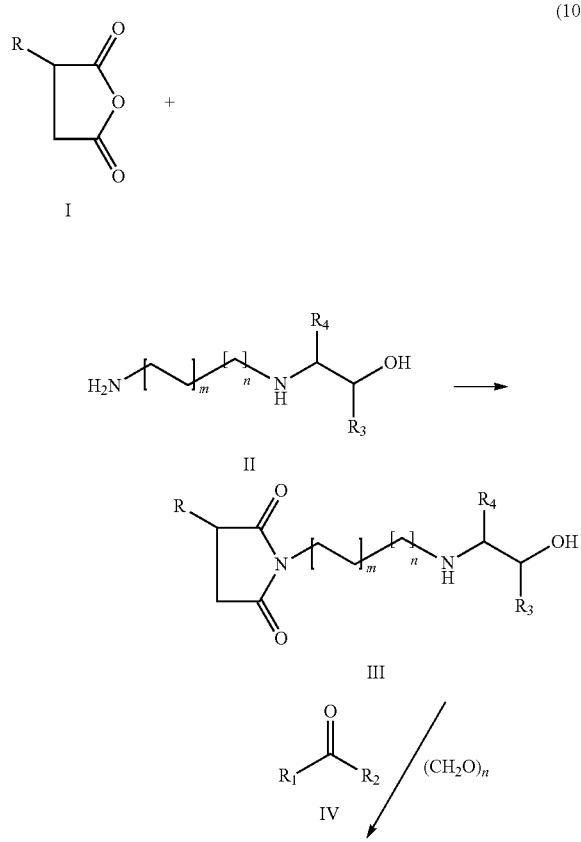

(10)

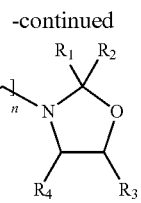

V

The first stage of the synthesis pathway consists in making a succinic polyalkyl or polyalkylene anhydride having the formula I react with a 2-(aminoalkylamino)-2,3-disubstituted-alcohol having the formula II, in order to obtain the corresponding polyalkyl or polyalkenyl N-hydroxyalkyl succinimides with the structural formula III. The molar ratio of succinic polyalkyl or polyalkylene anhydride to 2-(aminoalkylamino)-2,3-disubstituted-alcohol can vary within the range of 1:1 to 1:10, preferably within the range from 1:1 to 1:4, and the reaction may be carried out in the bulk substance or in presence of a hydrocarbon solvent, including preferably toluene, mixtures of xylene, o-xylene, m-xylene, p-xylene, kerosene, and turbo-fuel. The reaction time depends on the structure of the polyalkyl or polyalkylene succinic anhydride and the 2-(aminoalkylamino)-2,3-disubstituted-alcohol used as reactants, as well as on the temperature at which the reaction is carried out. Generally, the reaction time varies within the range from 1 to 24 hours, and the reaction temperature varies within the range from 80 to 200° C., preferably within the range from 120 to 180° C.

The polyalkyl or polyalkylene succinic anhydrides group R consists of polyisobutylene, polybutene, polyethylene, or polypropylene derivatives and its molecular weight varies within the range from 450 to 5000 Daltons; preferably, as an R substituent we have the polyisobutylene derivatives, with a molecular weight ranging from 450 to 2300. Typically, the polyalkylene succinic anhydrides are prepared as described in the U.S. Pat. No. 3,361,673 and U.S. Pat. No. 3,676,089 international patents, as well as in the MX 234498 national patent, whereas the polyalkyl succinic anhydrides can be prepared by catalytic hydrogenation of the corresponding polyalkylene succinic anhydrides, using palladium on carbon as a catalyst.

The 2-(aminoalkylamino)-2,3-disubstituted-alcohols preferred by the present invention include commercially available compounds or those that can be easily prepared by conventional methods. Among these we have: 2(2-aminoethylamino)ethanol, 2-(3-aminopropylamino)ethanol, 2-(4-aminobutylamino)ethanol, 2-(5-aminopentylamino)ethanol, 2-(6-aminohexylamino)ethanol, 2-(7-aminoheptylamino)ethanol, 2-(8-aminooctylamino)ethanol, 2-(9-aminononylamino)ethanol, 2-(10-aminodecylamino)ethanol, 2-(2-aminoethylamino)-1,2-dimethyl-ethanol, 2-(2-aminoethylamino)-2-methyl-ethanol, 1-methyl-2-(2-aminoethylamino)-ethanol, 2-(2-aminoethylamino)-1,2-dyphenil-ethanol, 2-(2-aminoethylamino)-2-phenil-ethanol, 1-phenyl-2-(2-aminoethylamino)-ethanol, 2-hydroxyl-3-(2-aminoethylamino)-propanol, and 2-hydroxymethyl-2-(2-aminoethylamino)ethanol.

The second stage of the synthesis pathway consists in making the corresponding polyalkyl or polyalkenyl N-hydroxyalkyl succinimides react with a compound having the structural formula IV, or paraformaldehyde, in order to obtain the corresponding oxazolidines derived from polyalkyl or polyalkenyl N-hydroxyalkyl succinimides with the structural formula V. The compounds with the structural formula IV appropriate for the present invention include commercially available aldehydes and ketones or those that can be easily prepared using conventional methods. The molar ratio of polyalkyl or polyalkenyl N-hydroxyalkyl succinimide to aldehyde, ketone or paraformaldehyde can vary within the range from 1:1 to 1:5, preferably within the range from 1:1 to 1:2, and the reaction may be carried out in the bulk substance or in the presence of an inert hydrocarbon solvent, preferably including toluene, mixtures of xylene, o-xylene, m-xylene, p-xylene, kerosene, and turbo-fuel. The reaction time depends on the structure of the polyalkyl or polyalkenyl N-hydroxyalkyl succinimide or the aldehyde or ketone used as reactants, as well as on the temperature and pressure at which the reaction is carried out. Generally, the reaction time varies within the range from 1 to 24 hours; the reaction temperature varies within the range from 60 to 200° C., preferably within the range from 100 to 180° C., and the pressure at which the reaction is carried out varies within the range from 60 to 760 mmHg, preferably within the range from 400 to 585 mm of Hg.

The aldehydes and ketones preferred by the present invention include ethanal, propanal, butanal, pentanal, hexanal, heptanal, octanal, nonyl aldehyde, decyl aldehyde, dodecyl aldehyde, tetradecyl aldehyde, hexadecyl aldehyde, octadecyl aldehyde, benzaldehyde, salicylaldehyde, 3-hydroxybenzaldehyde, 4-hydroxybenzaldehyde, o-tolualdehyde, m-tolualdehyde, p-tolualdehyde, o-anisaldehyde, m-anisaldehyde, p-anisaldehyde, 4-ter-butylbenzaldehyde, 4-butylbenzaldehyde, 4-ethylbenzaldehyde, 2-ethylbenzaldehyde, 4-propylbenzaldehyde, 2-propylbenzaldehyde, 4-phenoxybenzaldehyde, 3-phenoxybenzaldehyde, 4-formyl-benzene sulfonic acid, 2-formyl-benzene sulfonic acid, 2-biphenyl carboxyaldehyde, 4-biphenyl carboxyaldehyde, 2,3-dihydroxybenzaldehyde, 2,4-dihydroxybenzaldehyde, 2,5-dihydroxybenzaldehyde, 3,4-dihydroxybenzaldehyde, 3,5-dihydroxybenzaldehyde, 2-hydroxy-4-methoxybenzaldehyde, 2-hydroxy-5-methoxybenzaldehyde, 3-hydroxy-4-methoxybenzaldehyde, 2-hydroxy-3-methylbenzaldehyde, 2-hydroxy-5-methylbenzaldehyde, 4-hydroxy-3-methylbenzaldehyde, 1-naphthaldehyde, 2-naphthaldehyde, 2-hydroxy-1-naphthaldehyde, 4-hydroxy-1-naphthaldehyde, 2-methyl-1-naphthaldehyde, 4-methyl-1-naphthaldehyde, 2-methoxy-1-naphthaldehyde, 4-methoxy-1-naphthaldehyde, 6-methoxy-2-naphthaldehyde, acetone, 2-butanone, benzophenone, 2,2'-dihydroxybenzophenone, 2,4-dihydroxybenzophenone, acetophenone, and 4'-tert-butyl acetophenone.

The compounds of the present invention and their formulations are useful as additives in crude oil and products derived thereof, in order to prevent and control asphaltenes' deposition in wells, ducts and refining plants. The concentration of additive necessary to control the deposition of asphaltenes depends on the type of crude oil or product derived thereof, and on the presence of other additives in the fuel.

Generally, the concentration of the compounds object of this invention in crude oil varies within the range from 1 to 2000 parts per million (ppm), preferably from 1 to 500 ppm. When other types of additives that control the deposition of organic compounds are present, a lesser amount of the additive can be used.

The oxazolidines of the present invention can be formulated as a concentrate using inert organic solvents having a boiling point within the range of 75 to 300° C., preferably hydrocarbon solvents, such as benzene, toluene, mixtures of xylenes, o-xylene, m-xylene and p-xylene, diesel, kerosine, turbo-fuel, branched and non-branched aliphatic alcohols having in their structures from 3 to 10 carbon atoms, such as isoporopanol, butanol, and pentanol, as well as mixtures of hydrocarbon solvents with branched and non-branched aliphatic alcohols. The quantity of active in the formulation ranges from 10 to 90 wt. %, preferably from 25 to 75 wt. %.

Performance Tests

The evaluation of the performance as asphaltenes' precipitation or deposition inhibitors and as asphaltenic aggregates' dispersants of the compounds object of the present invention, was carried out through five different tests: I) Measurement of the onset of the precipitation of asphatenes by change of pressure to bottom of well temperature and pressure conditions (inhibitory effect at oilfield conditions); II) Measurement of the onset of the precipitation of asphatenes by adding a precipitant at ambient temperature and pressure conditions (inhibitory precipitation effect at ambient conditions); III) Measurement of the mass deposited on metallic surfaces by means of the effect of an electrostatic field (deposition inhibitory effect); IV) Measurement of the dispersion of asphaltenes in crude petroleum-heptane mixtures (asphaltenic aggregates' dispersant effect); V) Measurement of the dispersion of asphaltenic sediments in mixtures with hexane.

I). Measuring Test of the Asphaltene Precipitation Onset by Change of Pressure to Bottom-of-Well Temperature and Pressure Conditions.

This test consists in isothermally expanding a preserved live crude petroleum sample from an oilfield or higher pressure, to such a pressure, that the onset of precipitation is perfectly defined. In this test, the expansion that the petroleum undergoes while ascending from the oilfield through the production pipeline is experimentally reproduced in the interior of a variable volume balance visual cell, shown in FIG. (2). As the pressure decreases and the petroleum sample expands, the opacity of the sample is measured by recording the intensity of the laser beam that crosses the sample relative to the pressure. As the pressure in the cell is decreased, the sample is expanded and its density is reduced, resulting in a decrease of the sample's opacity, which is recorded as a continuous and gradual increase of the intensity of the light that crosses the sample; when the formation of precipitate begins, the size and quantity of the particles in the sample are augmented, producing an increase in the sample's opacity and a decrease in the light able to cross it, which is observed as a change in the slope of the transmitted light potency vs. pressure curve (as shown in FIG. (3). The pressure value where this slope change is observed is defined as the point of initiation or onset of the asphaltenes' precipitation.

This methodology was described by Hammami et al. (Energy & Fuels 2000, 14, 14) for purposes of determination of the asphaltenes' precipitation onset in preserved crude oils samples. In the same sense, the effect of the additive inhibitor of asphaltene precipitation can be then determined by comparing the onset of crude oil without additive against the onset of crude oil dosed with the inhibitor additive aggregated.

The additive's inhibitory efficiency is determined taking as a reference the pressure at the beginning of the precipitation obtained from a preserved crude petroleum sample without additive, according to the following formula:

$$\text{Efficiency} = \frac{\text{Onset with Inhibitor} - \text{Onset without Inhibitor}}{\text{Onset without Inhibitor}}$$

Test conditions:
   Constant temperature: 155° C.
   Initial pressure: 100 MPa
   Final pressure: That at which the potency of the transmitted light decreases to values within the range of 1.0E-13 Watts.
   Volume of the preserved crude petroleum sample: 25 cm³.
   Inhibitor dosage: 2000 ppm (mg/L).
   Mixture time prior to each test: 2 hours.
   Preserved live sample (samples A and B): Crude petroleum sample taken in the bottom of the well, where the fluid is found in a single liquid phase without asphaltenes precipitated and with all its gas dissolved. It is called preserved because its pressure condition remains constant from the moment sampling to the moment of the test, due to the sampler and the storing cylinders mechanisms, which, by means of a piston and a nitrogen or other pressurized fluid chamber maintain a higher or equal pressure than the original pressure of the petroleum at the sampling point, accounting for the pressure variations due to temperature changes during its extraction, transportation and storage.

II). Measuring Test of the Asphaltene Precipitation Onset by Adding a Precipitant at Room Temperature and Pressure Conditions.

This test, which is a variation of the test described in the above section, consists in adding continuously, stirring constantly, at constant temperature and pressure, an asphaltene precipitating agent, in this case n-heptane, a sample of dead crude petroleum up to such a volume, that the onset of the precipitation is perfectly defined. This is performed in an equilibrium cell with a detector of solids shown in FIG. 4). The opacity changes in the mixture are observed throughout the test, recording the potency changes of the laser beam that crosses the sample, with respect to the volume of precipitant added, obtaining a potency vs. volume graph, as the one shown in FIG. (5). The start or onset of precipitation is defined as the volume of precipitant required per cubic centimeter of petroleum sample in order to initiate the precipitation of asphaltenes, which corresponds to the maximum point of the potency vs. volume curve, from which the quantity of light that crosses the sample starts to decrease continuously due to the presence of asphaltene precipitates. The efficiency of the additive is determined by taking as a reference the pressure at the beginning of the precipitation obtained from a preserved crude petroleum sample without additive, according to the following formula:

$$\text{Efficiency} = \frac{\text{Onset with Inhibitor} - \text{Onset without Inhibitor}}{\text{Onset without Inhibitor}}$$

Onset=Volume of precipitant corresponding to the maximum light potency/Sample volume Test conditions:
   Temperature: 35° C.
   Pressure: 0.0774 MPa
   Crude petroleum sample volume: 25 cm³
   Precipitant addition rate: 0.167 cm³/min
   Inhibitor dosage: 2000 ppm (mg/L)
   Mixing time prior to the start of each test: 2 hours
   Sample (samples C and D): Crude petroleum sample taken at well mouth level and submitted to a process of agitation in an open container to eliminate dissolved gases, and centrifugation and decantation to remove suspended solids (dead crude petroleum sample).

III). Test to Measure the Deposition of Mass on Metallic Surfaces by Means of the Effect of an Electrostatic Field.

This test consists in inducing the deposition of organic material on a metallic surface by means of applying an electrostatic field. The asphaltenic aggregates suspended in crude oil, in spite of not possessing a net electrical charge, due to their electronic density, are sensitive to electrostatic fields having certain intensity, which generates an electrostatic charge in them that induces their deposition on the plate connected to the positive pole of the potentiometer. A Teflon array, having two parallel metallic stainless steel plates separated by 5 mm, is introduced to each cell; the system is balanced at the test temperature, and the electric field is applied during 24 h, by the end of which, the plates (previously weighted) are removed from the cells and left to drain for 8 h, to afterwards be weighted and the quantity of deposited material to be determined. The efficiency of the compound is determined relative to the difference between the mass deposited on the plate from the sample without inhibitor, the reference, and the mass deposited from a crude sample with inhibitor.

$$\text{Efficiency} = \frac{\text{Reference mass deposition} - \text{Inhibitor mass deposition}}{\text{Reference mass deposition}}$$

Test conditions:
   Temperature: 50° C.
   Pressure: 0.0774 MPa (ambient)
   Crude petroleum sample volume: 500 cm³
   Voltage: 800 V
   Amperage: 3000 mA
   Inhibitor dosage: 1000 ppm (mg/L)
   Sample: Same crude petroleum samples used on test II, samples C and D.

IV) Test to Measure Asphaltenes Dispersed in a Heptane-Crude Petroleum Mixture by Visible-UV Spectroscopy. Measurement of the Dispersion of Asphaltenes in Heptane-Crude Petroleum Mixtures.

This test is based on the fact that asphaltenes are soluble in aromatic hydrocarbons, but not in aliphatic hydrocarbons, such as heptane. The dispersant capacity of the compounds of interest can be assessed by dissolving the crude petroleum in an aromatic dissolvent, then adding the aliphatic precipitant, in order to provoke precipitation. Since asphaltenes absorb energy within the Visible-UV spectrum, an approximated measure of the precipitated asphaltene can be obtained by measuring the absorption within the Visible-UV spectrum of the resulting supernatant fluid. Variations of this Visible-UV spectroscopy-based methodology have been used to measure the remaining concentration of asphaltenes in solution, a measure of the dispersant efficiency of determined chemical products, among which U.S. Pat. No. 6,313,367B1 and US 20040039125 A1 American patent applications can be mentioned.

The procedure that has been designed for this specific test consists in:
   Prepare a 1:1 solution of dead crude petroleum (samples C and D) in toluene.
   Prepare a dispersant additive solution of 0.2 g of the dispersant formulation in 5 mL of toluene.
   In a test tube, add 9.5 mL of heptane and 0.5 mL of the dispersant solution, in order to reach a dispersant concentration (dosage) of 2000 ppm (mg/l), mix well and add 0.1 ml of the crude-toluene solution, stir vigorously for 15 seconds and let rest for 24 hours.

Prepare the reference in toluene (reference A): Pour into a test tube 10 mL of toluene, then add 0.1 mL of the crude-toluene solution, stir vigorously and let rest for 24 hours.

After the rest period, take 3 mL of the dispersion supernatant, being careful not to take the asphaltene settled in the bottom; afterwards, filter using a 0.45 mm syringe filter and transfer to the cell of the Vis-UV spectrophotometer.

Measure the maximum absorbance at a 700 nm wavelength.

Calculate the ratio of absorbances using the following equations in order to establish the relative efficiency of the dispersant:

$$\text{Efficiency} = \frac{\text{Absorbance of the Dispersion}}{\text{Reference A Absorbance}}$$

If the asphaltene is entirely dispersed by the effect of the additive, the absorbance of the dispersion should be equal to that of the reference, yielding an efficiency of one. Based on this, the efficiency range lies between 0 and 1.

V) Measurement of the Dispersion of Asphaltenic Sediments in Mixtures with Hexane.

This test is based on the fact that asphaltenes are insoluble in aliphatic hydrocarbons, such as n-hexane. The working sample is the sediment separated from the crude petroleum of interest. The dispersant capability of the compounds of interest can be assessed by adding to the sediment a volume in excess of n-hexane in order to promote the most precipitation possible, then measuring the volume of the sediment that was not dispersed. However, it is not expected for the compound to dissolve the sediment, but to disperse it in small particles that can be maintained in suspension during the test period. The procedure of this test consists in:

To obtain a sample of sediment: Centrifuge the crude petroleum of interest for 30 minutes at 3000 rpm.

To prepare the reference: Weigh 0.4 g of the sediment in a 15 mL conical test tube with graduation every 0.1 mL, and pour into the tube 15 mL of hexane, mix first with a spatula, dispersing the sediment, and then submit the mixture to agitation in an ultrasound bath during 5 minutes.

Prepare a solution of the dispersant formulation by mixing 0.03 g of it in 15 mL of hexane, up to a concentration of 2000 ppm.

Weigh 0.4 g of the sediment in a conical test tube as the one described above, 15 mL of the solution prepared according to the previous point, mix first using a spatula, dispersing the sediment, and then submit the mixture to agitation in an ultrasound bath during 5 minutes, let rest during 6 hours.

Measure the volume of sediment using the tube graduation.

Calculate the efficiency of the dispersant in relation with the reference without dispersant.

$$\text{Efficiency} = \frac{\text{Reference sediment } vol. - \text{Sediment } vol. \text{ with dispersant}}{\text{Reference sediment } vol.}$$

EXAMPLES

Tables 1 to 3 provide the properties of samples A, B, C, D and F of preserved live crude petroleum that were used in the performance tests of the asphaltene inhibitor-dispersant additive of the present invention.

Tables 4 to 8 show the results obtained on the performance tests of some examples of the formulations object of the present invention, as well as three asphaltene inhibitor-dispersants marketed nationwide to be applied in the petroleum industry: Commercial Product 1, Commercial Product 2, and Commercial Product 3. Additionally, tables 1 to 3 show the properties and compositions of the crude petroleum and sediment samples used in the performance tests.

The examples evaluated comply with the following characteristics:

Examples 1-8

The main active component is an oxazolidine derived from a polyalkenyl N-hydroxyalkyl succinimide, containing in its structure a polyalkenyl group having an average molecular weight within the range of 700 to 1500 Daltons; wherein the value of m can range from 1 to 3; the value of n can range from 0 to 1; R1, R2, R3 and R4 are any of these functional groups: —H, —$CH_2(CH_2)_4B$, —$C_6H_3DE$ or —$C_{10}H_4FG$. The amount of the main active component in these formulations is within the range of 25 to 45% wt. The rest of the formulation in % wt. is constituted by an inert organic dissolvent that, in the case of examples 1, 3, 5 and 7 is Xylene, and in examples 2, 4, 6 and 8 is diesel.

TABLE 1

Properties of the preserved live crude petroleum samples A and B used in test I.

|  | Sample A | Sample B |
|---|---|---|
| Density (g/cm$^3$) at 155° C. and 56.97 MPa | 0.785 | 0.776 |
| Bubble Pressure (MPa) a 155° C. | 16.85 | 16.96 |
| Composition of the oil without gas Fraction (% wt.) | | |
| Fraction of saturated hydrocarbons | 46.89 | 46.48 |
| Fraction of aromatic hydrocarbons | 33.07 | 34.34 |
| Fraction of polar hydrocarbons (resins) | 17.30 | 17.74 |
| Asphaltenes | 2.74 | 1.44 |

TABLE 2

Composition of samples C and D used in tests II to IV.

|  | Sample C | Sample D |
|---|---|---|
| Density at 25° C. and ambient pressure Composition (% wt.) | 0.852 | 0.845 |
| Crystallizable paraffins | 6.13 | 5.75 |
| Fraction of saturated hydrocarbons | 54.80 | 63.66 |
| Fraction of aromatic hydrocarbons | 23.57 | 24.11 |
| Fraction of saturated hydrocarbons (resins) | 21.21 | 11.68 |
| Asphaltenes | 0.41 | 0.56 |

TABLE 3

Composition of Samples E and F

| Composition (% wt.) | Sample E (sediment obtained from sample C) | Sample F (sediment obtained from sample D) |
|---|---|---|
| Toluene insolubles | 0.64 | 0.11 |
| Crystallizable paraffins | 18.97 | 18.35 |
| Fraction of saturated hydrocarbons | 54.67 | 51.55 |
| Fraction of aromatic hydrocarbons | 13.23 | 17.36 |
| Fraction of polar hydrocarbons (resins) | 17.30 | 17.09 |
| Asphaltenes | 14.80 | 14.00 |

TABLE 4

Test I Results.

| | Sample A (onset MPa) | Sample B (onset MPa) | Efficiency on A | Efficiency on B |
|---|---|---|---|---|
| Preserved live crude petroleum | 93.2 | 62 | | |
| Example 1 | 28.8 | — | 0.69 | — |
| Example 3 | — | 48.9 | — | 0.21 |
| Example 4 | — | 48.9 | — | 0.21 |
| Example 5 | 33.9 | — | 0.64 | — |
| Example 7 | — | 30.3 | — | 0.51 |
| Example 8 | — | 30.3 | — | 0.51 |
| Commercial Product 1 | 49 | 38.1 | 0.47 | 0.39 |

TABLE 5

Test II Results.

| | Sample C Onset (cm³ precipitant/cm³ of sample) | Sample D Onset (cm³ precipitant/cm³ of sample) | Efficiency on C | Efficiency on D | Average efficiency |
|---|---|---|---|---|---|
| Dead crude petroleum | 0.52 | 0.52 | | | |
| Example 1 | 1 | 0.96 | 0.92 | 0.85 | 0.88 |
| Example 2 | 1 | 0.96 | 0.92 | 0.85 | 0.88 |
| Example 3 | 0.89 | 1.17 | 0.71 | 1.25 | 0.98 |
| Example 5 | 1.04 | 1.22 | 1.00 | 1.35 | 1.17 |
| Example 6 | 1.04 | 1.22 | 1.00 | 1.35 | 1.17 |
| Example 8 | 1.04 | 1.18 | 1.00 | 1.27 | 1.13 |
| Commercial Product 2 | 0.9 | 0.62 | 0.73 | 0.19 | 0.46 |
| Commercial Products | 0.77 | 0.68 | 0.48 | 0.31 | 0.39 |

TABLE 6

Test III Results.

| | Sample D Deposited mass (g) | Efficiency |
|---|---|---|
| Dead crude petroleum | 310.3 | |
| Example 1 | 0 | 1.00 |
| Example 2 | 0 | 1.00 |
| Example 3 | 44.4 | 0.86 |
| Example 4 | 44.4 | 0.86 |
| Example 5 | 0 | 1.00 |
| Example 6 | 0 | 1.00 |
| Example 7 | 0 | 1.00 |
| Commercial Product 2 | 0 | 1.00 |
| Commercial Product 3 | 287 | 0.08 |
| Commercial Product 1 | 0 | 1.00 |

TABLE 7

Test IV Results.

| | Sample C Efficiency (absorbances ratio) | Sample D Efficiency (absorbances ratio) | Average efficiency |
|---|---|---|---|
| Crude petroleum solution in toluene | 1 | 1 | 1 |
| Example 1 | 0.58 | 0.42 | 0.50 |
| Example 2 | 0.58 | 0.42 | 0.50 |
| Example 3 | 0.58 | 0.49 | 0.54 |
| Example 5 | 0.57 | 0.52 | 0.55 |
| Example 6 | 0.57 | 0.52 | 0.55 |
| Example 7 | 0.51 | 0.37 | 0.44 |
| Commercial Product 2 | 0.58 | 0.49 | 0.54 |
| Commercial Product 3 | 0.52 | 0.52 | 0.52 |

TABLE 8

Test V Results.

| | Sample E (mL) | Sample F (mL) | Efficiency on E | Efficiency on F | Average efficiency |
|---|---|---|---|---|---|
| Sediment separated from crude petroleum | 2.4 | 2.5 | | | |
| Example 1 | 0.45 | 0.75 | 0.81 | 0.70 | 0.76 |
| Example 2 | 0.45 | 0.75 | 0.81 | 0.70 | 0.76 |
| Example 3 | 0.55 | 0.83 | 0.77 | 0.67 | 0.72 |
| Example 4 | 0.55 | 0.83 | 0.77 | 0.67 | 0.72 |
| Example 5 | 0.5 | 0.7 | 0.79 | 0.72 | 0.76 |
| Example 6 | 0.5 | 0.7 | 0.79 | 0.72 | 0.76 |
| Example 8 | 0.4 | 0.75 | 0.83 | 0.70 | 0.77 |
| Commercial Product 2 | 0.45 | 0.5 | 0.81 | 0.80 | 0.81 |
| Commercial Product 3 | 1.9 | 1.5 | 0.21 | 0.40 | 0.30 |

As can be observed from the results presented on tables 4 to 6, the performance shown by the examples evaluated of the compounds object of the present invention clearly demonstrates their functionality as inhibitors of the precipitation and deposition of asphaltenes. Additionally, it can be observed that the evaluated examples have a superior efficacy as inhibitors compared to the commercial products selected and evaluated under the same conditions. The only exceptions were the formulations of examples 3 and 4, which exhibited a slightly inferior performance with respect to the commercial product on test I as inhibitors of the precipitation of asphaltenes at high temperature and pressure conditions, whereas on test III, as inhibitors of the deposition on metallic surfaces, their performance was surpassed by two of the three commercial products assessed.

Regarding the functionality of the evaluated examples of the compounds object of the present invention as dispersants of asphaltenic aggregates and sediments, this was clearly demonstrated, based on the efficiency achieved by said compounds, which is shown on tables 7 and 8. On test IV, where their functionality as asphaltene dispersants is evaluated in petroleum, toluene or heptane solutions, the performance of the considered examples is comparable or superior to that of the commercial products, except for example 7, whose performance resulted slightly inferior. In the case of test V, where their capacity as asphaltenic sediments dispersants is evaluated, the performance of the evaluated products was high, although slightly inferior compared to one of the commercial products, but very superior to that of the second commercial product.

The set of results of the performance tests allows to establish clearly the capability of the compounds object of the present invention to act as both asphaltene inhibitors and dispersants to be used in crude oils and products derived thereof in order to control fouling and/or clogging problems occurring in the production, transportation, refining and storage processes in the petroleum industry, just as it was stated in the field of this invention. These products distinguish themselves with respect to the commercial products evaluated for this double functionality because, even when one of them demonstrated a comparable or superior capability on the dispersion tests, it was clearly surpassed, as were both the other products, on the precipitation and deposition tests.

That which is claimed is:

1. An asphaltene dispersant-inhibitor additive formulation, said additive formulation comprising an oxazolidine derived from polyalkyl or polyalkenyl N-hydroxyalkyl succinimides as a main active component and inert organic solvents, said oxazolidine having the formula:

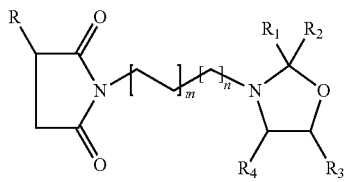

wherein R is a polyalkyl or polyalkenyl group having an average molecular weight within the range from 450 to 5000 Daltons; m is an integer having values between 1 and 5; n is an integer between 0 and 1; and $R_1$, $R_2$, $R_3$ and $R_4$ are independent radicals represented by the groups —H, —CH$_2$(CH$_2$)$_4$B, —C$_6$H$_3$DE or —C$_{10}$H$_4$FG;
wherein:
A is an integer between 0 and 8,
B is a group selected among —H, —NH$_2$, —OH, —COOH;
and D, E, F and G are independent radicals, selected from the groups consisting of:
—H, —CH$_3$, —CH$_2$CH$_3$, —CH$_2$CH$_2$CH$_3$, —CH$_2$(CH$_2$)$_2$CH$_3$, —(CH$_3$)$_3$, C$_6$H$_5$, —NH$_2$, —OH, —OCH$_3$, OCH$_2$CH$_2$OH, OCH(CH$_3$)CH$_2$OH, and OC$_6$H$_5$—COOH, —SO$_3$,
wherein said additive formulation when present in crude oil inhibits precipitation and disperses asphaltenes in crude oil at reservoir conditions.

2. Additive formulations according to claim 1, wherein the quantity of the main active component in the formulations is in the range of 10 to 90% wt.

3. Additive formulations according to claim 1, wherein the weight ratio of inert organic solvents to main active component ranges from 1:9 to 9:1.

4. Additive formulations according to claim 1, wherein the organic solvent is an alcohol having from 3 to 10 carbon atoms.

5. Additive formulations according to claim 4, wherein said alcohols are isopropanol, butanol or pentanol.

6. A mixture comprising an additive formulation and crude oil, where the additive formulation is according to claim 1, and where said oxazolidine is included in said crude oil at concentrations within the range from 1 to 2000 parts per million.

7. Additive formulations according to claim 1, wherein group R is derived from polyisobutylene, polybutene, polyethylene, or polypropylene, and its molecular weight varies within the range from 450 to 5000 Daltons.

8. Additive formulations according to claim 1, wherein substituents $R_3$ and $R_4$ come from a 2-(aminoalkylamino)-2,3-disubstituted-alcohol.

9. Additive formulations according to claim 1, wherein groups $R_1$ and $R_2$ are derived from a paraformaldehyde, an aldehyde, or a ketone.

10. Additive formulations according to claim 9, wherein the aldehydes are aromatic or aliphatic.

11. Additive formulations according to claim 10, wherein the aliphatic aldehyde is linear or branched.

12. Additive formulations according to claim 9, wherein the ketones are aromatic or aliphatic.

13. Additive formulations according to claim 9, wherein the aliphatic ketones are linear or branched.

14. Additive formulations according to claim 1, wherein the quantity of the main active component in the formulations is in the range of 25 to 75% wt.

15. Additive formulations according to claim 1, wherein the weight ratio of inert organic solvents to main active component ranges from 1:3 to 3:1.

16. Additive formulations according to claim 1, wherein the inert organic solvents have a boiling point within the range of 75 to 300° C.

17. Additive formulations according to claim 16, wherein the inert organic solvents have a boiling onset temperature within the range of 75 to 300° C.

18. Additive formulations according to claim 1, wherein the inert organic solvents are selected from the group consisting of benzene, toluene, mixtures of xylene, o-xylene, p-xylene, turbo fuel, diesel kerosene; branched and non-branched aliphatic alcohols, inert hydrocarbon solvents having boiling points within the range of gasoline and diesel, inert hydrocarbon and organic solvents having boiling points within the range of 75 to 300° C., and mixtures of hydrocarbon solvents with branched and non-branched aliphatic alcohols.

19. A mixture comprising an additive formulation of claim 1 and crude oil, wherein the oxazolidine is included in said crude oil at a concentration within the range of from 5 to 500 parts per million.

20. A composition comprising: (1) an asphaltene dispersant-inhibitor additive formulation, said additive formulation including a compound having the formula

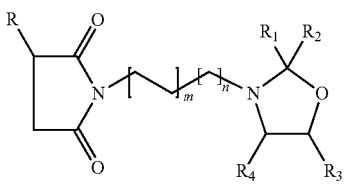

Zone Name: wherein R is a polyalkyl or polyalkenyl group having an average molecular weight within the range from 450 to 5000 Daltons; m is an integer having values between 1 and 5; n is an integer between 0 and 1; and $R_1$, $R_2$, $R_3$ and $R_4$ are independent radicals represented by the groups —H, —$CH_2(CH_2)_AB$, —$C_6H_3DE$ or —$C_{10}H_4FG$;

wherein:

A is an integer between 0 and 8,

B is a group selected among —H, —$NH_2$, —OH, —COOH;

and D, E, F and G are independent radicals, selected from the groups:

—H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_5$—COOH, —$SO_3$;

dispersed in an organic solvent in a ratio of 1:9 to 9:1; and (2) crude oil, where said additive and crude oil are mixed in a weight ratio sufficient to disperse, inhibit precipitation and deposition of asphaltenes in said crude oil at reservoir conditions.

21. The composition of claim 20, wherein said additive formulation is mixed with said crude oil in a weight ratio of 0.005:500 to 10:500.

22. The composition of claim 21, wherein
said additive formulation is present in said crude oil in a weight ratio of 0.005:500 to 2.5:500.

23. A method of inhibiting the precipitation and deposition of asphaltenes in crude oil comprising:

adding additive formulation to crude oil in an amount effective to inhibit precipitation of asphaltenes from said crude oil at reservoir conditions where crude oil is considered as live, and at pressures below its onset point, and to inhibit deposition of asphaltenes on surfaces carrying said crude oil at atmospheric conditions where crude oil is considered dead oil, wherein said additive formulation comprises an oxazolidine derived from polyalkyl or polyalkylene N-hydroxyalkyl succinimides wherein said oxazolidine has the general formula

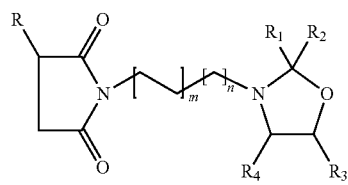

wherein R is a polyalkyl or polyalkenyl group having an average molecular weight within the range from 450 to 5000 Daltons; m is an integer having values between 1 and 5; n is an integer between 0 and 1; and $R_1$, $R_2$, $R_3$ and $R_4$ are independent radicals represented by the groups —H, —$CH_2(CH_2)_AB$, —$C_6H_3DE$ or —$C_{10}H_4FG$;

wherein:

A is an integer between 0 and 8,

B is a group selected among —H, —$NH_2$, —OH, —COOH;

and D, E, F and G are independent radicals, selected from the groups:

—H, —$CH_3$, —$CH_2CH_3$, —$CH_2CH_2CH_3$, —$CH_2(CH_2)_2CH_3$, —$(CH_3)_3$, $C_6H_5$, —$NH_2$, —OH, —$OCH_3$, $OCH_2CH_2OH$, $OCH(CH_3)CH_2OH$, $OC_6H_5$—COOH, —$SO_3$, wherein said additive formulation is dispersed in an organic solvent in a weight ratio of 1:9 to 9:1.

24. The method of claim 23, further comprising adding said additive formulation containing said oxazolidine to said crude oil in a weight ratio of 0.005:500 to 2.5:500.

* * * * *